United States Patent
Hrecznyj et al.

(10) Patent No.: US 11,964,064 B2
(45) Date of Patent: Apr. 23, 2024

(54) VEHICLE RECEPTACLE FOR RECHARGING AND SANITIZING MOBILE ELECTRONICS

(71) Applicant: FORD GLOBAL TECHNOLOGIES, LLC, Dearborn, MI (US)

(72) Inventors: Michael Hrecznyj, Livonia, MI (US); John Van Wiemeersch, Novi, MI (US); Vivekanandh Elangovan, Canton, MI (US)

(73) Assignee: FORD GLOBAL TECHNOLOGIES, LLC, Dearborn, MI (US)

( * ) Notice: Subject to any disclaimer, the term of this patent is extended or adjusted under 35 U.S.C. 154(b) by 511 days.

(21) Appl. No.: 17/215,263

(22) Filed: Mar. 29, 2021

(65) Prior Publication Data

US 2022/0305154 A1    Sep. 29, 2022

(51) Int. Cl.
*H02J 7/00*      (2006.01)
*A61L 2/10*      (2006.01)
*A61L 2/24*      (2006.01)
*B60L 53/12*      (2019.01)

(52) U.S. Cl.
CPC .............. *A61L 2/10* (2013.01); *A61L 2/24* (2013.01); *B60L 53/12* (2019.02)

(58) Field of Classification Search
USPC ............... 320/106, 107, 108, 109, 110, 112
See application file for complete search history.

(56) References Cited

U.S. PATENT DOCUMENTS

| 8,964,405 B2 * | 2/2015 | La Porte .............. A61L 2/10 361/807 |
| 9,124,124 B2 | 9/2015 | Van Wiemeersch et al. |
| 9,197,094 B2 | 11/2015 | Van Wiemeersch et al. |
| 9,783,102 B2 | 10/2017 | Salter et al. |

FOREIGN PATENT DOCUMENTS

| JP | H10308802 | * | 11/1998 |
| KR | 101517694 B1 | | 5/2015 |
| KR | 20190036201 | * | 1/2019 |
| KR | 20190036201 A | | 4/2019 |
| WO | 2015122611 A1 | | 8/2015 |

OTHER PUBLICATIONS

Utilimedic UV8LEF, Dedicated in-car phone sanitizer with wired and wireless Qi charging, https://www.crutchfield.com/S-a3KiNFDfJof/p_070UV8LED/Utilimedic-EV8LED.html.

* cited by examiner

*Primary Examiner* — Brian Ngo
(74) *Attorney, Agent, or Firm* — Frank L. Lollo; MacMillan, Sobanski & Todd, LLC

(57) ABSTRACT

A vehicle apparatus charges and sanitizes a mobile device. The mobile device has an inductive power receiver coil for wireless charging. A storage bin in the vehicle (such as a center console or a glove compartment) has a movable lid. A tray of the charging/sanitizing apparatus is adapted to receive a side surface of the mobile device so that a majority of the side surface is suspended from the tray by a gap. A first wireless power link is configured to inductively charge the mobile device from the tray to the power receiver coil. A plurality of ultraviolet emitters are disposed at a plurality of locations inside the storage bin to illuminate an exterior of the mobile device when the movable lid is closed. At least some of the ultraviolet emitters are also inductively powered.

18 Claims, 4 Drawing Sheets

VEHICLE RECEPTACLE FOR RECHARGING AND SANITIZING MOBILE ELECTRONICS

CROSS REFERENCE TO RELATED APPLICATIONS

Not Applicable.

STATEMENT REGARDING FEDERALLY SPONSORED RESEARCH

Not Applicable.

BACKGROUND OF THE INVENTION

The present invention relates in general to wireless recharging of mobile devices in a motor vehicle, and, more specifically, to simultaneous charging and ultraviolet sanitizing of a mobile device.

Mobile devices, such as cell phones, watches, and digital cameras typically employ rechargeable batteries that must be periodically recharged. Conventionally, these electronic devices have been charged using a physical connection to an electrical charger via a wire. More recently, wireless charging devices such as inductive chargers have become available to charge the battery without any physical wire connection between the mobile electronic device and a charging device. Inductive chargers may be used which generate a magnetic field through the use of inductive coils in order to transfer the electric energy from the charging device to a receiver on a battery or in the mobile device. Inductive chargers have been proposed for use on vehicles in various locations within the cockpit of the vehicle, typically near the driver and other passengers, for the sake of convenience to allow easy access to the devices.

Industry standards for wireless inductive charging have been defined, which has led to increasing availability of wireless chargers and the mobile devices that use them. For instance, a popular wireless charging solution is known as Qi® charging technology. One or more transmission coils within or below a support surface are energized when a mobile device having one or more receiving coils is placed on the support surface. In a transportation vehicle such as a car or truck, a charging surface may be provided within a storage bin (e.g., in a center console between left and right front seats).

Another aspect of use of mobile devices relates to the desire of users to regularly sanitize (e.g., disinfect) their devices in order to reduce the spread of pathogens that may lead to sickness or disease. Sanitation solutions have included disinfecting wipes/sprays and anti-bacterial soaps, for example. The use of such sanitation products sometimes increases to the point that there are shortages of cleaning supplies, so that procurement can be a challenge. It would be desirable to provide a sustainable solution for sanitizing a mobile device while in the vehicle.

Irradiation by ultraviolet light is an alternative process for sanitizing surfaces. UV sanitizers can be found not only in hospital settings but also in consumer applications such as HVAC systems, vacuum cleaners, air cleaners, portable hand wands, water purifiers, and phone case sanitizers. Incorporating a UV sanitizer in a passenger cabin of a vehicle raises many challengers. Prolonged exposure of UV light can be damaging to most plastics, human skin, and eyes, especially in the UV-C bandwidth which is normally required for disinfection. Thus, use of a UV sanitizer in a vehicle would necessitate an enclosed compartment (e.g., in the center storage console or a glove compartment) to protect the consumer during use. In addition, the material in these compartments would have to resist UV degradation for the life of the vehicle in order to prevent mechanical and visual degradation.

SUMMARY OF THE INVENTION

In one aspect of the invention, a vehicle apparatus is provided for charging and sanitizing a mobile device which has an inductive power receiver coil. The apparatus comprises a storage bin having a movable lid. A tray of the apparatus is adapted to receive a side surface of the mobile device so that a majority of the side surface is suspended from the tray by a gap. A first wireless power link is configured to inductively charge the mobile device from the tray to the power receiver coil. A plurality of ultraviolet emitters are disposed at a plurality of locations inside the storage bin to illuminate an exterior of the mobile device when the movable lid is closed. At least some of the ultraviolet emitters are also inductively powered.

In addition to cellphones as shown in some preferred embodiments, the present invention may be applicable to any mobile devices adapted for wireless charging, including digital cameras, supplemental powerpacks, watches, fitness trainers, GPS/navigational units, hearing aids, or music players.

DETAILED DESCRIPTION OF PREFERRED EMBODIMENTS

Figure 1:
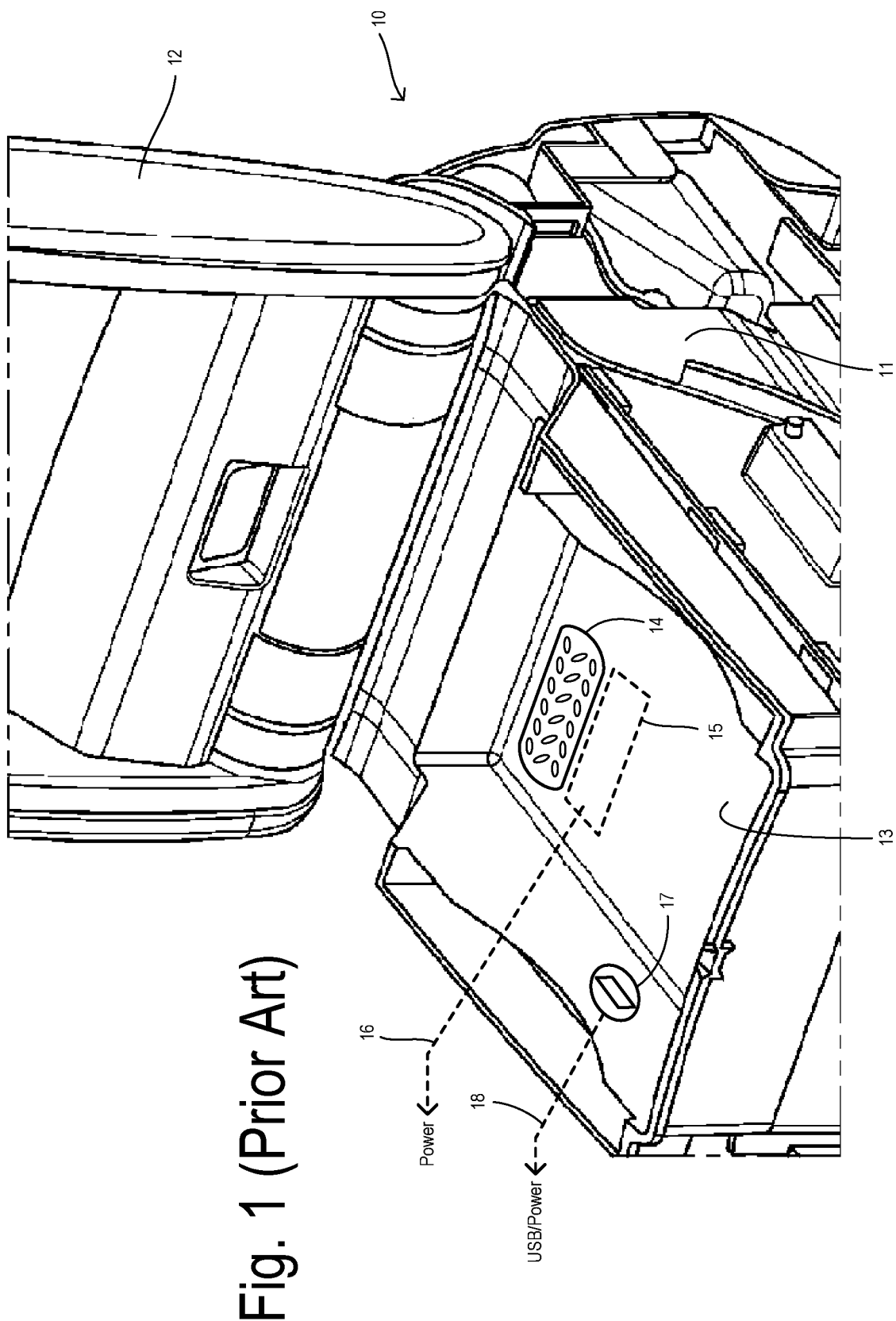
FIG. 1 is a perspective view of a prior art center console including an inductive charging surface for a mobile device.

FIG. 1 shows a center console 10 having a base 11 and a movable lid 12 that pivots on a hinge to selectably open and close console 10. When open, a shelf or tray 13 is accessible which includes an inductive charging region 14. Region 14 may include various features for identifying its location to a user (e.g., contrasting colors, lines, symbols, or indentations) or for holding a mobile unit in place (e.g., bumper, ridges, or a pocket matching the range of sizes for mobile cellphones). Beneath and/or embedded in tray 13 juxtaposed with region 14 is a power transmitter 15 which receives a supply voltage via vehicle wiring 16. Power transmitter 15 may include one or more inductive transmission coils according to a known inductive charging protocol (e.g., Qi® charging). The interior of console 10 may further include a wired power outlet such as a USB port 17 for powering devices brought into the console 10. USB port 17 receives a supply voltage via vehicle wiring 18.

By configuring power transmitter 15 and region 14 to accommodate various kinds of mobile devices, by adopting a common inductive charging protocol (e.g., Qi®), and by providing a wired charge source via USB, a user of the vehicle is able to charge a wide range of mobile devices while driving. Moreover, lid 12 can be closed with the mobile device(s) residing on tray 13 so that they can be safely retained in an enclosed area during driving.

The present invention enables simultaneous charging and sanitizing mobile devices using UV radiation (most preferably, UV-C radiation). In some embodiments of the invention, mobile devices being charged and sanitized can be used/operated while stowed in a charger/sanitizer. For example, a cellphone or other wireless device can be linked to vehicle electronics using a Bluetooth®, Ultra-Wideband (UWB), or a WiFi link. The mobile device is covered in order to shield any vehicle occupants from exposure to the sanitizing ultraviolet light.

Figure 2:
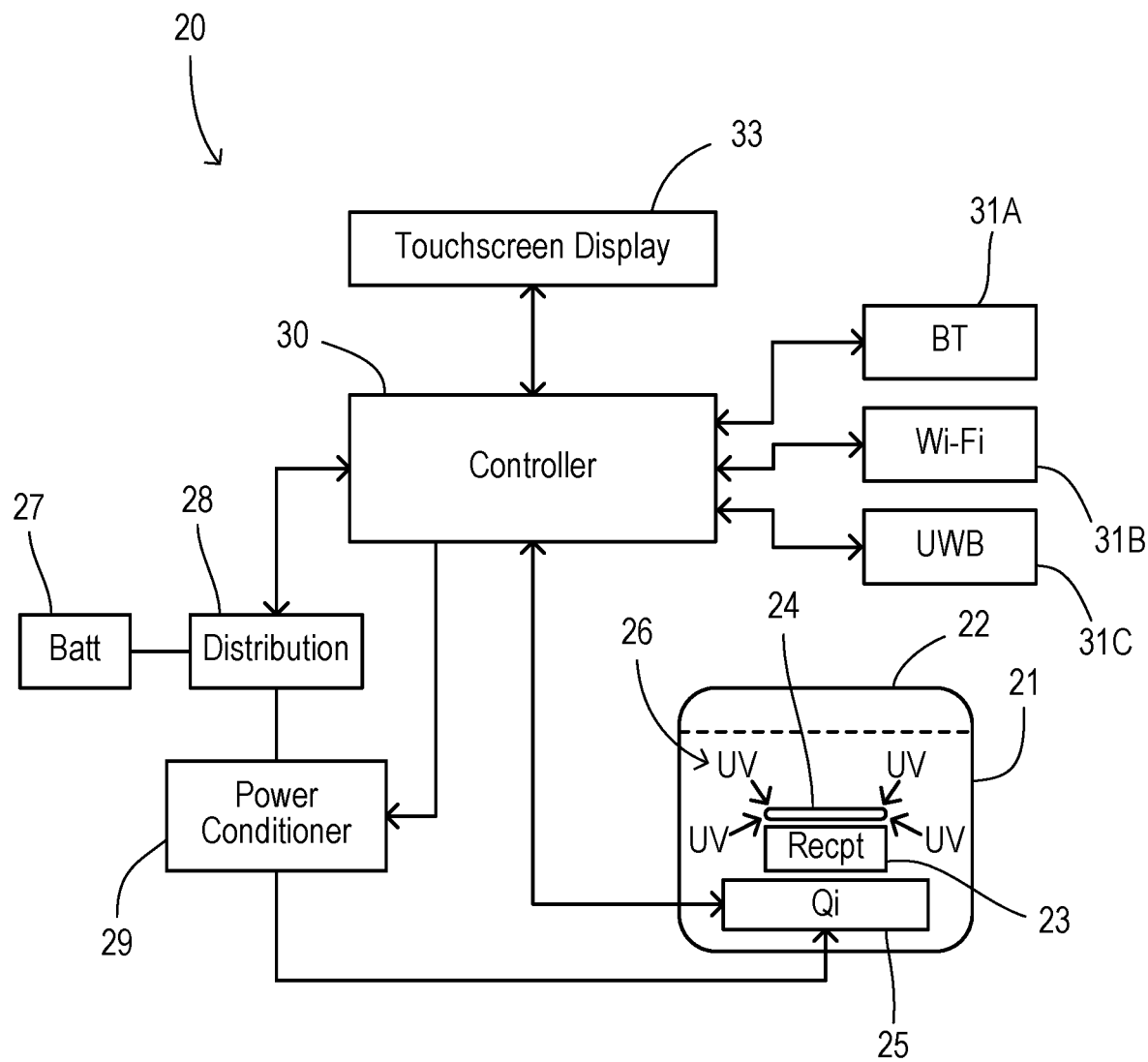
FIG. 2 is a block diagram showing an example of a charging/sanitizing system of the invention.

FIG. 2 shows a vehicle apparatus 20 for use in a passenger cabin of a motor vehicle, such as a car or truck. A storage bin 21 (e.g., a center console, a glove compartment, or other container) has a movable lid 22 covering an internal chamber having a receptacle 23 for receiving a mobile device 24. Receptacle 23 may include a tray (e.g., flat, horizontal surface) or other supporting surface configured such that mobile device 24 has a majority of its bottom surface facing receptacle 23 separated by a small gap which enables UV light to be directed against the bottom surface. For example, a pattern of protuberances (e.g., raised posts or bumps) may extend upward from the top surface of receptacle 23 (e.g., positioned near the four corners of a rectangular bottom surface of the mobile device) having a height which creates a gap which is large enough to distribute UV light all around mobile device 24 from UV emitters 26 and small enough to maintain inductive coupling with a power transmission coil 25 incorporated in or beneath receptacle 23 in a manner known in the art. A battery 27 or other electric power source feeds an electrical distribution system 28. A power conditioner 29 converts a DC voltage from distribution system 28 into an alternative signal for driving transmission coil 25 (e.g., using a standard Qi® protocol).

A controller 30 manages operation of the charger/sanitizer via connections to UV-C LEDs 26, power conditioner 29, and other components (e.g., sensors) described below. Controller 30 may also communicate with mobile device 24 via a wired link or via a wireless link using a Bluetooth® transceiver 31A, a WiFi transceiver 31B, and/or a UWB transceiver 31C. A touchscreen display 33 is coupled to controller 30 for providing a human interface for controlling and monitoring the charging and sanitizing functions. Various options for controlling and monitoring the operations will be included in the following detailed embodiments.

Simultaneous charging and sanitizing functions can be obtained using appropriate devices which are either designed into a particular model of vehicle (e.g., factory installed) or as an insert which is designed to interface with one or more pre-existing vehicles (e.g., through the addition of aftermarket units). For example, a drop-in vehicle accessory unit may be configured to be placed into a center console or other covered storage bin. The drop-in unit adds UV sanitation functions together with wireless charging without requiring modification to an existing storage bin. The unit may be compatible with a vehicle charger standard and may obtain power to operate UV LEDs and to charge a mobile device from an existing inductive charging mat in the storage bin or from a vehicle USB plug or 12V powerpoint adapter.

In some embodiments, UV illumination may be halted due to a sensed motion of a customer or a bin lid (e.g., using IR and/or capacitive sensors). There may be a hard on/off switch to initiate charging (which may start immediately if a mobile device is requesting power for charging), but UV sanitation may only start after proximity or motion sensors determine that the lid is closed and/or a customer is not present (in a position where they could be impacted by the UV illumination).

UV light emitting diodes (LEDs) may be placed above and below the suspended mobile device to give maximum phone coverage and save the user an added step of flipping over the device to expose another side. In addition to on/off controls, a user may select a duration for a sanitation cycle or other parameters using dedicated controls and/or indicators on a charging/sanitizing unit or using a vehicle interface (e.g., touchscreen). Displayed information or feedback (e.g., on/off, sanitation cycle interrupted, or sanitation cycle complete) can be provided with dedicated indicators or via the vehicle interface. Especially when constructed as a drop-in accessory, the charging/sanitizing apparatus may include a Bluetooth® transceiver to enable it to pair (e.g., BLE pairing) with the vehicle for expanded HMI control/feedback via a touchscreen.

Figure 3:
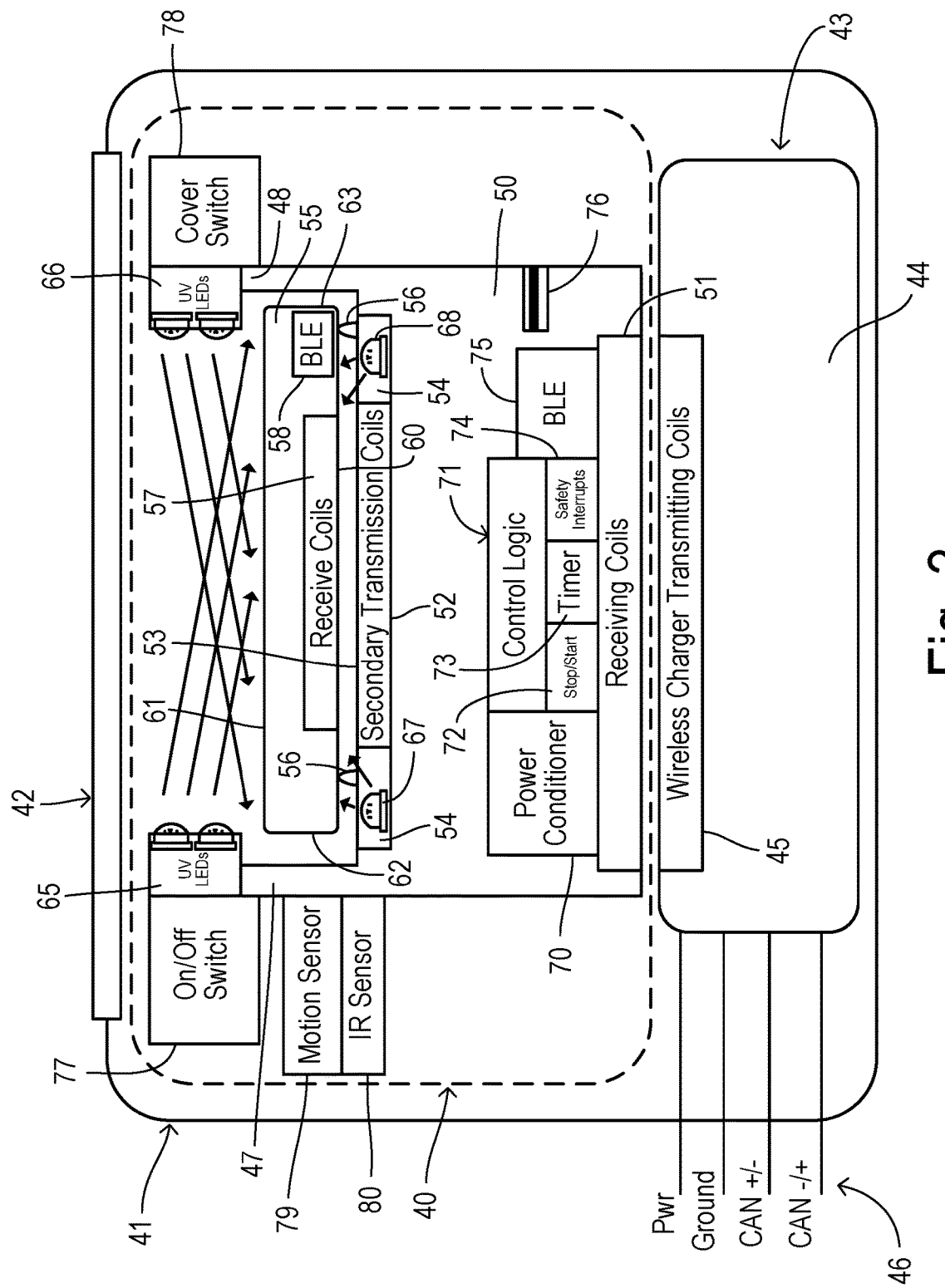
FIG. 3 is a block diagram depicting a first embodiment of a charging/sanitizing apparatus in the form of a drop-in accessory unit adapted for placement in a center console of a vehicle.

Referring to FIG. 3, a drop-in vehicle accessory 40 is configured to be inserted into a vehicle center console or storage bin 41 which has a lid 42 movable between opened and closed positions. In this example, bin 41 incorporates an inductive charger 43 having a charging base 43 with embedded transmitting coils 45. Base 43 is wired via terminals 46 to a system power supply and ground and to a multiplex bus (e.g., a CAN bus) to communicate with one or more controllers and a vehicle HMI.

Drop-in accessory unit 40 has a main body 50 configured to dock into storage bin 41. Body 50 has a power receiver for receiving electrical power from the vehicle. The power receiver can be an inductive connection via one or more power receiving coils 51 which are contained in body 50 and configured to be juxtaposed with transmitting coils 45 when accessory unit 40 is properly docked in bin 41. A power conditioner 70 in body 50 conditions the received power to operate electronic components within accessory unit 40 (e.g., UV LEDs). Power conditioner 70 also supplies an inductive charging signal (e.g., a Qi® signal) to a secondary transmission coil(s) 52 in order to inductively transfer power to a power receiving coil 57 in a mobile device 55 or sleeve attached to mobile device 55. Body 50 includes a tray surface 53 adapted to receive a side surface 60 (e.g., bottom surface) of mobile device 55. Tray upper surface 53 has a pattern of a plurality of protuberances 56 (e.g., raised posts or bumps) so that a majority of bottom surface 60 is suspended from tray 53 by a gap. The gap is sufficiently small that a first wireless power link for inductively charging mobile device 55 operates efficiently to transfer energy from transmission coil(s) 52 to power receiver coil(s) 57, and yet large enough to convey UV-C light to irradiate a majority of bottom surface 60. As used herein, a majority of surface 60 means at least more than half the surface and preferably as much as 98% of the surface or more is exposed (i.e., not in contact with tray 53). Preferably, mobile device 55 has upper surface 61 and side surfaces 62 and 63 which may be fully irradiated by UV-C sanitizing light since they are not in contact with other surfaces. In embodiments using Bluetooth® (e.g., BLE) communication, mobile device 55 contains a BLE transceiver 58.

For ultraviolet sanitizing, body 50 further supports a plurality of UV-C LEDs 65, 66, 67, and 68 disposed at a plurality of locations from which they can illuminate an exterior of mobile device 55. Body 50 has vertical wings 47 and 48 supporting groups of UV-C LEDs 65 and 66, respectively, to irradiate at least surfaces 61, 62, and 63 of mobile device 55. Tray 53 or other portions of body 50 disposed lower than bottom surface 60 retain LEDs 67 and 68 in an orientation that directs UV-C light toward surface 60. LEDs 67 and 68 may be mounted in recesses 54, for example. In some embodiments, one or more of the LEDs may be covered by or embedded in UV transmissive materials. The LEDs within tray 53 may be interspersed with transmission coil(s) 52.

LEDs 65, 66, 67, and 68 receive power from main power conditioner 70 within accessory unit 40. Preferably, they are inductively powered via a second wireless power link formed by power receiving coils 51 juxtaposed with power transmission coils 45 when unit 40 is docked within bin 41 (e.g., the inductive power transfer originally intended for directly charging a mobile phone is utilized to power the sanitizing LEDs and control electronics as well as charging a mobile device placed in an upper horizontal surface or tray of the drop-in accessory unit). For use in vehicles without an inductive charger in a storage bin, unit 40 may include a USB input circuit 76 configured to receive electrical power from a wired USB power outlet incorporated storage bin 41 (e.g., via a USB cable which is not shown).

Body 50 further contains a control logic 71 including a start/stop circuit 72, a timer 73, and safety interrupts 74 which help ensure that LEDs 65, 66, 67, and 68 are energized to produce UV light only when requested by a user and only when movable lid 42 is closed. Logic circuit 71 may be configured to communicate with a vehicle user interface via a wireless communication channel which may be provided by a BLE transceiver 75. Various commands and/or data may be exchanged with the user interface for managing the charging and sanitizing of the mobile device, as well as providing wireless access to the main functions of mobile device 55 (e.g., cellular phone calls).

Body 50 further contains a manual on/off switch(es) 77 for controlling charging and/or sanitizing functions without reliance on a vehicle interface. A sensor 78 coupled to control logic 71 determines the opened state or closed state of movable lid 42. Sensor 78 can be a cover switch which mechanically interacts with lid 42 to change the state of a switch when lid 42 is fully closed. Other non-contact switches may also be used, such as an accelerometer or shock sensor. Safety interrupt circuit 74 in control logic 71 inhibits actuation of UV LEDs 65-68 when the opened state is detected.

As a backup safety measure, proximity of a user (e.g., a hand) to accessory unit 40 may be sensed (e.g., indicating that lid 42 is open). Proximity sensors may include a motion sensor 79 and/or an IR sensor 80 coupled to control logic 71. For example, when sensors 79 or 80 detect incursion of an object within a predetermined proximity of accessory unit 40, then control logic 71 inhibits the sanitizing function.

It should be noted that FIG. 3 is not shown to scale. The vertical height of accessory unit 40 is exaggerated for clarity. An actual height of such a unit for installation into a center console may be about 1.0 to 1.5 inches, for example.

Figure 4:
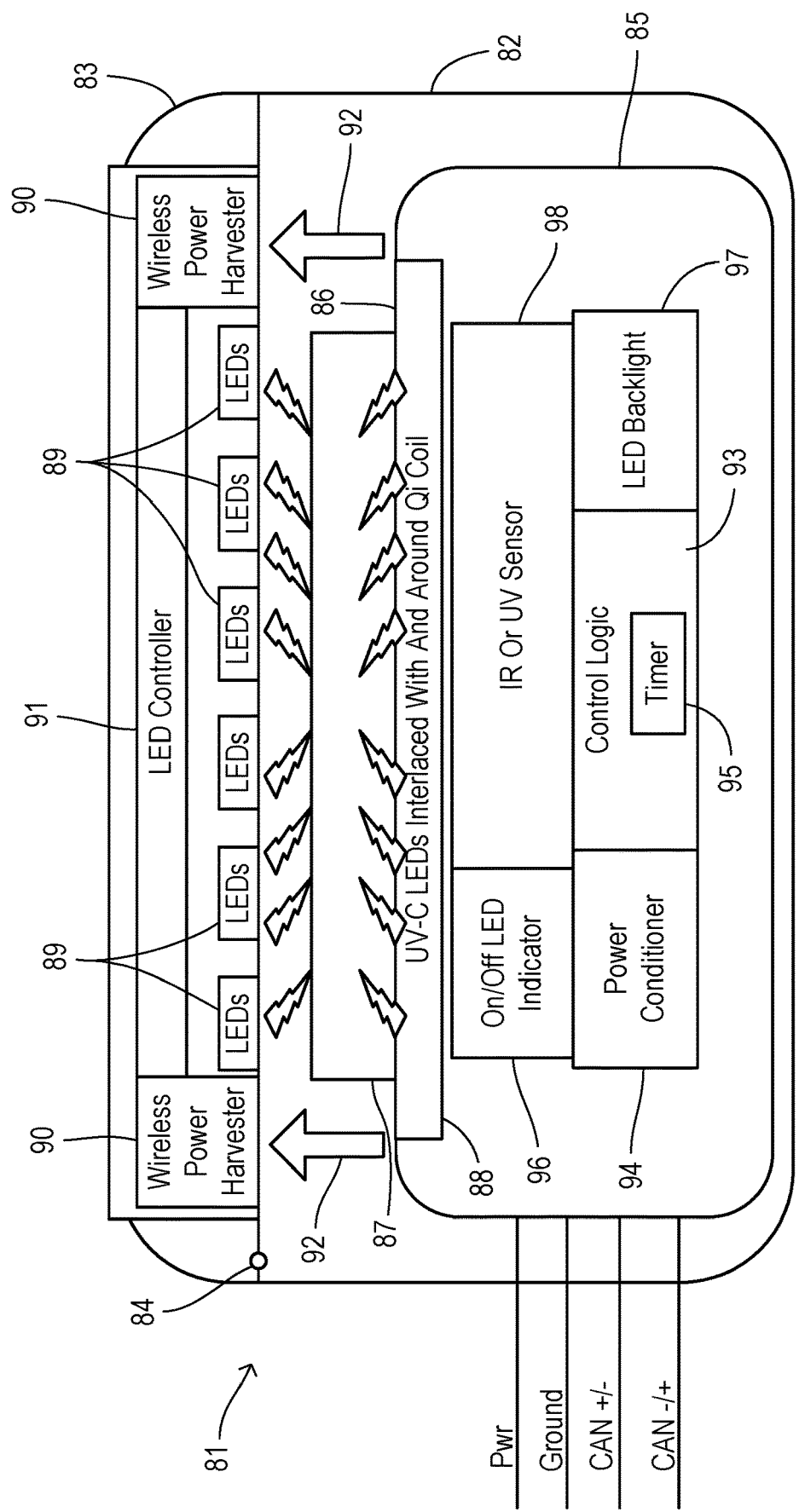
FIG. 4 is a block diagram depicting a second embodiment of a charging/sanitizing apparatus integrated within a center console of a vehicle.

FIG. 4 shows an alternative embodiment (likewise exaggerated in height) wherein charging and sanitizing functions are integrated with (e.g., designed into) a storage bin 81. Bin 81 includes a base 82 and a movable lid 83 attached to base 82 by a hinge 84. A charger/sanitizer body 85 is disposed in an inner chamber of bin base 82 and provides a tray surface 86 to receive a mobile device 87. Tray surface 86 has an embedded pad 88 containing UV-C LEDs interlaced with (e.g., dispersed around and between) inductive power transmitting (e.g., Qi-compatible) coil(s). UV-C LEDs in pad 88 are configured to irradiate a bottom surface (and optionally some side surfaces) of mobile device 87. For irradiating top and side surfaces of mobile device 87, a plurality of UV-C LEDs 89 are mounted in the movable lid. In order to avoid the difficulties of routing power supply and/or control wires from base 82 into lid 83, a wireless power harvester 90 is mounted with LEDs 89 in lid 83. Power harvester 90 may be comprised of one or more power receiver coils juxtaposed with the power transmitting coils in pad 88, forming a second wireless power link 92 which supplies electrical power to an LED controller 91 and to UV-C LEDs 89 mounted in movable lid 83. Link 92 also couples data/commands to LED controller 91 to ensure that ultraviolet illumination occurs only under the appropriate conditions.

Charger/sanitizer body 85 further contains control logic 93 for managing charging and sanitizing functions and a power conditioner 94 for converting DC power from a vehicle power bus to an alternating signal to drive the inductive transmitting coils. Control logic 71 functions similarly to the embodiment of FIG. 3, and may include a timer 95 in order to provide a timed sanitizing cycle. Device status and related information (e.g., on/off, sanitation interrupted, and sanitation cycle complete) can be displayed to a user with an on/off LED indicator 96 and/or a backlit LED display 97. Sensing of an open/closed state of lid 83 and proximity of a user can be obtained using a sensor or group of sensors 98 (e.g., an IR and/or UV sensor). Operational settings (e.g., automatic sanitizing upon closing of the lid/door) can be adjusted using a vehicle HMI (not shown) or display 97 can include a touchscreen input, for example.

LED interlacing with power transmission coils in pad 88 helps provide thermal mitigation for the LEDs. Upper hinge cover 83 mounts LEDs 89 with an even displacement in order to efficiently radiate a sufficient UV-C intensity to the top side of mobile device 87. The interspersed LEDs in pad 88 achieves 360° UV and avoids the need for flipping the mobile device for a full UV sanitation effect. Lid 83 does not need any external wiring or a physical electrical connection to the vehicle, thereby increasing the electrical robustness, reducing/eliminating packaging of the wiring, and avoiding wire harness warranty issues of broken wires due to flexing when lid 83 opens and closes.

Communication and UV coordination between lid 83 and body 85 can also be achieved via wireless communication (e.g., BLE transceivers). The lid mounted controller 91 communicates its status (on/off) and position (open or closed). Lid 83 may include various sensors (not shown) to determine its open or closed state, such as an ajar switch, g-sensor, light sensor, or a circuit for measuring the signal strength of communication/power within link 92. The presence of mobile device 87 can be detected, if desired, by measuring the visible or UV light intensity with sensors placed in or around pad 88. Such object detection can be used to automate the UV sterilization and/or to save LED device lifetimes.

In some embodiments, the charging/sanitizing apparatus may be self-contained by providing command/control elements and user status indicator/display within storage bin 81. More preferably, the apparatus may be connected to a vehicle HMI (e.g., touchscreen) via a wired multiplex bus (e.g., CAN bus) or a wireless communication link (e.g., BLE, WiFi). This increases the ability of command/control and feedback to user.

What is claimed is:

1. Vehicle apparatus for charging and sanitizing a mobile device having an inductive power receiver coil, comprising:
   a storage bin having a movable lid;

a tray adapted to receive a side surface of the mobile device so that a majority of the side surface is suspended from the tray by a gap;

a first wireless power link configured to inductively charge the mobile device from the tray to the power receiver coil;

a plurality of ultraviolet emitters disposed at a plurality of locations inside the storage bin, wherein the ultraviolet emitters are inductively powered via a second wireless power link and arranged to illuminate an exterior of the mobile device when the movable lid is closed.

2. The vehicle apparatus of claim 1 further comprising a first power transmission coil disposed in the tray in proximity to the mobile device;

wherein the first wireless power link inductively transfers power from the first power transmission coil in the tray to the power receiving coil in the mobile device.

3. The vehicle apparatus of claim 2 wherein the tray is formed in an upper horizontal surface of a drop-in accessory unit which is configured to insert into the storage bin over a second power transmission coil built into a wall of the storage bin which receives electrical power from a wired power bus, wherein at least some of the ultraviolet emitters are mounted on the drop-in accessory unit, and wherein the drop-in accessory unit is comprised of:

a second power receiver coil juxtaposed with the second power transmission coil to form the second wireless power link, wherein electrical power from the second wireless power link is coupled to the first wireless power link and to the ultraviolet emitters mounted on the drop-in accessory.

4. The vehicle apparatus of claim 3 wherein the drop-in accessory unit further comprises an input circuit configured to receive electrical power from a wired power outlet incorporated in the storage bin.

5. The vehicle apparatus of claim 3 wherein the drop-in accessory unit further comprises a controller powered from the second wireless power link, wherein the controller manages charging and sanitizing of the mobile device, and wherein the controller is configured to communicate with a vehicle user interface via a wireless communication channel.

6. The vehicle apparatus of claim 5 further comprising:

a first sensor coupled to the controller and configured to detect an opened state or a closed state of the movable lid;

wherein the controller inhibits actuation of the ultraviolet emitters when the opened state is detected.

7. The vehicle apparatus of claim 6 further comprising:

a second sensor coupled to the controller and configured to detect incursion of an object within a predetermined proximity of the accessory unit;

wherein the controller inhibits actuation of the ultraviolet emitters when the incursion of the object is detected.

8. The vehicle apparatus of claim 1 wherein at least some of the ultraviolet emitters are mounted in the movable lid, and wherein the vehicle apparatus further comprises:

a second power receiver coil juxtaposed with the first power transmission coil to form the second wireless power link, wherein electrical power from the second wireless power link is coupled to the ultraviolet emitters mounted in the movable lid.

9. The vehicle apparatus of claim 8 wherein at least some of the ultraviolet emitters are mounted in the tray and are powered from a wired power bus in the storage bin.

10. The vehicle apparatus of claim 1 wherein the mobile device is comprised of a mobile phone.

11. A vehicle accessory unit for charging and sanitizing a mobile device, comprising:

a body configured to dock into a storage bin in an interior cabin of a vehicle, wherein the storage bin has a movable lid and an integrated transmitting coil of a charging base;

a power receiver in the body for wirelessly receiving electrical power from the integrated transmitting coil;

a tray adapted to receive a side surface of the mobile device so that a majority of the side surface is suspended from the tray by a gap;

a first power transmission coil disposed in the body adjacent the tray configured to inductively charge the mobile device when located in the tray;

a plurality of ultraviolet emitters disposed in the body at a plurality of locations directing ultraviolet radiation within the tray to illuminate an exterior of the mobile device when the movable lid is closed, wherein the ultraviolet emitters are powered via the electrical power received wirelessly by the power receiver.

12. The vehicle accessory unit of claim 11 wherein the tray is formed in an upper horizontal surface of the body.

13. The vehicle accessory unit of claim 11 wherein:

the body is configured to overlie the integrated transmitting coil which is built into a wall of the storage bin and which receives electrical power from a wired power bus of the vehicle; and the power receiver is comprised of a power receiver coil juxtaposed with the integrated transmitting transmission coil.

14. The vehicle accessory unit of claim 11 further comprising:

a controller powered by the electrical power received by the power receiver, wherein the controller manages charging and sanitizing of the mobile device, and wherein the controller is configured to communicate with a vehicle user interface via a wireless communication channel.

15. The vehicle accessory unit of claim 14 further comprising:

a first sensor disposed on the body and coupled to the controller, wherein the first sensor is configured to detect an opened state or a closed state of the movable lid;

wherein the controller inhibits actuation of the ultraviolet emitters when the opened state is detected.

16. The vehicle accessory unit of claim 15 further comprising:

a second sensor coupled to the controller and configured to detect incursion of an object within a predetermined proximity of the accessory unit;

wherein the controller inhibits actuation of the ultraviolet emitters when the incursion of the object is detected.

17. The vehicle accessory unit of claim 11 wherein the mobile device is comprised of a mobile phone.

18. The vehicle accessory unit of claim 11 wherein the ultraviolet emitters are comprised of UVC LEDs affixed to the body.

* * * * *